United States Patent
Zack et al.

(10) Patent No.: US 9,433,741 B2
(45) Date of Patent: Sep. 6, 2016

(54) CUSTOM ADJUSTABLE PATIENT INTERFACE DEVICE

(71) Applicant: KONINKLIJKE PHILIPS N.V., Eindhoven (NL)

(72) Inventors: Alicia Marie Zack, Pittsburgh, PA (US); Robert William Baiko, Jr., Pittsburgh, PA (US); Daniel James Miller, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 308 days.

(21) Appl. No.: 14/356,228

(22) PCT Filed: Oct. 26, 2012

(86) PCT No.: PCT/IB2012/055916
§ 371 (c)(1),
(2) Date: May 5, 2014

(87) PCT Pub. No.: WO2013/068872
PCT Pub. Date: May 16, 2013

(65) Prior Publication Data
US 2014/0345621 A1    Nov. 27, 2014

Related U.S. Application Data

(60) Provisional application No. 61/556,397, filed on Nov. 7, 2011.

(51) Int. Cl.
*A61M 16/06* (2006.01)
*A61M 16/00* (2006.01)

(52) U.S. Cl.
CPC ......... *A61M 16/0605* (2014.02); *A61M 16/06* (2013.01); *A61M 16/0616* (2014.02); *A61M 2016/0661* (2013.01); *A61M 2207/00* (2013.01); *Y10T 29/49826* (2015.01)

(58) Field of Classification Search
CPC .......... A61M 16/06; A61M 16/0605; A61M 16/0616; A61M 2016/0661; A61M 2207/00; A61M 16/0057; A61M 16/0488; A61M 16/0611; A61M 16/0622; A61M 16/0633; A61M 16/0644; A61M 16/0683; A61M 16/0694; A61M 16/08; A61M 16/0816; A61M 16/0825; A61M 16/0858; A61M 2205/42; A61M 2210/0618; Y10T 29/49826; A62B 18/02; A62B 18/025; A62B 18/08; A62B 18/084; Y10S 128/912
USPC ........... 128/200.24, 202.27, 204.21, 205.25, 128/206.12, 206.16, 206.21, 206.24, 128/206.26, 206.27, 206.28, 207.11, 128/207.13, 912
See application file for complete search history.

(56) References Cited

U.S. PATENT DOCUMENTS

2007/0125385 A1    6/2007 Ho

FOREIGN PATENT DOCUMENTS

WO    WO2008028014 A2    3/2008

*Primary Examiner* — Annette Dixon
(74) *Attorney, Agent, or Firm* — Michael W. Haas

(57) ABSTRACT

A patient interface device (8) includes a cushion member (16) structured to engage a face of a patient when the patient interface device is donned by a patient, and a frame assembly (14), wherein the cushion member is coupled to the frame assembly. The frame assembly including a main frame member (18) having a plurality of pocket members (32) provided therein, and a plurality of peg members (20) coupled to the main frame member, wherein each peg member includes an arm member (42) that is received and held within a respective one of the pocket members at a user selectable position, and where in movement of the peg members relative to the main frame member adjusts a size and/or shape of the patient interface device.

16 Claims, 8 Drawing Sheets

CUSTOM ADJUSTABLE PATIENT INTERFACE DEVICE

CROSS-REFERENCE TO RELATED APPLICATIONS

This patent application claims the priority benefit under 35 U.S.C. §371 of international patent application no. PCT/IB2012/055916, filed Oct. 26, 2012, which claims the priority benefit under 35 U.S.C. §119(e) of U.S. Provisional Application No. 61/556,397 filed on Nov. 7, 2011, the contents of which are herein incorporated by reference.

BACKGROUND OF THE INVENTION

1. Field of the Invention

The present invention relates to patient interface devices for transporting a gas to and/or from an airway of a user, and, in particular, to a patient interface device that may be adjusted in a custom manner to accommodate different patient facial geometries.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

For such patient interface devices, a key engineering challenge is to balance patient comfort against mask stability and mask to face seal. This is particularly true in the case of treatment of OSA, where such patient interface devices are typically worn for an extended period of time. As a patient changes sleeping positions through the course of the night, masks tend to become dislodged, and the seal can be broken. A dislodged mask can be stabilized by increasing strapping force, but increased strapping force tends to reduce patient comfort. This design conflict is further complicated by the widely varying facial geometries that a given mask design needs to accommodate. As a result, the ability to accommodate a wide range of facial geometries is important in terms of seal and comfort of patient interface devices.

SUMMARY OF THE INVENTION

Accordingly, it is an object of the present invention to provide a patient interface device that overcomes the shortcomings of conventional patient interface devices. This object is achieved according to one embodiment of the present invention by providing patient interface device system that includes a custom adjustable frame assembly for selectively changing the size and/or shape of the patient interface device.

It is yet another object of the present invention to provide a method of adjusting patient interface device that overcomes the disadvantages associated with conventional patient interface devices. This object is achieved by providing a method that enables the size and/or shape of the patient interface device to be customized by the patient.

In one embodiment, a patient interface device is provided that includes a cushion member structured to engage a face of a patient when the patient interface device is donned by a patient, and a frame assembly, wherein the cushion member is coupled to the frame assembly. The frame assembly including a main frame member having a plurality of pocket members provided therein, and a plurality of peg members coupled to the main frame member, wherein each peg member includes an arm member that is received and held within a respective one of the pocket members at a user selectable position, and wherein movement of the peg members relative to the main frame member adjusts a size and/or shape of the patient interface device.

In another embodiment, a method of customizing a patient interface device is provided, wherein the patient interface device includes a cushion member and a frame assembly, the cushion member being coupled to the frame assembly. The frame assembly includes a main frame member having a plurality of pocket members provided therein, and a plurality of peg members coupled to the main frame member. The method of this embodiment includes, for each of the peg members, inserting an arm member of the peg member into a respective one of the pocket members and moving the arm member to a user selectable position.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
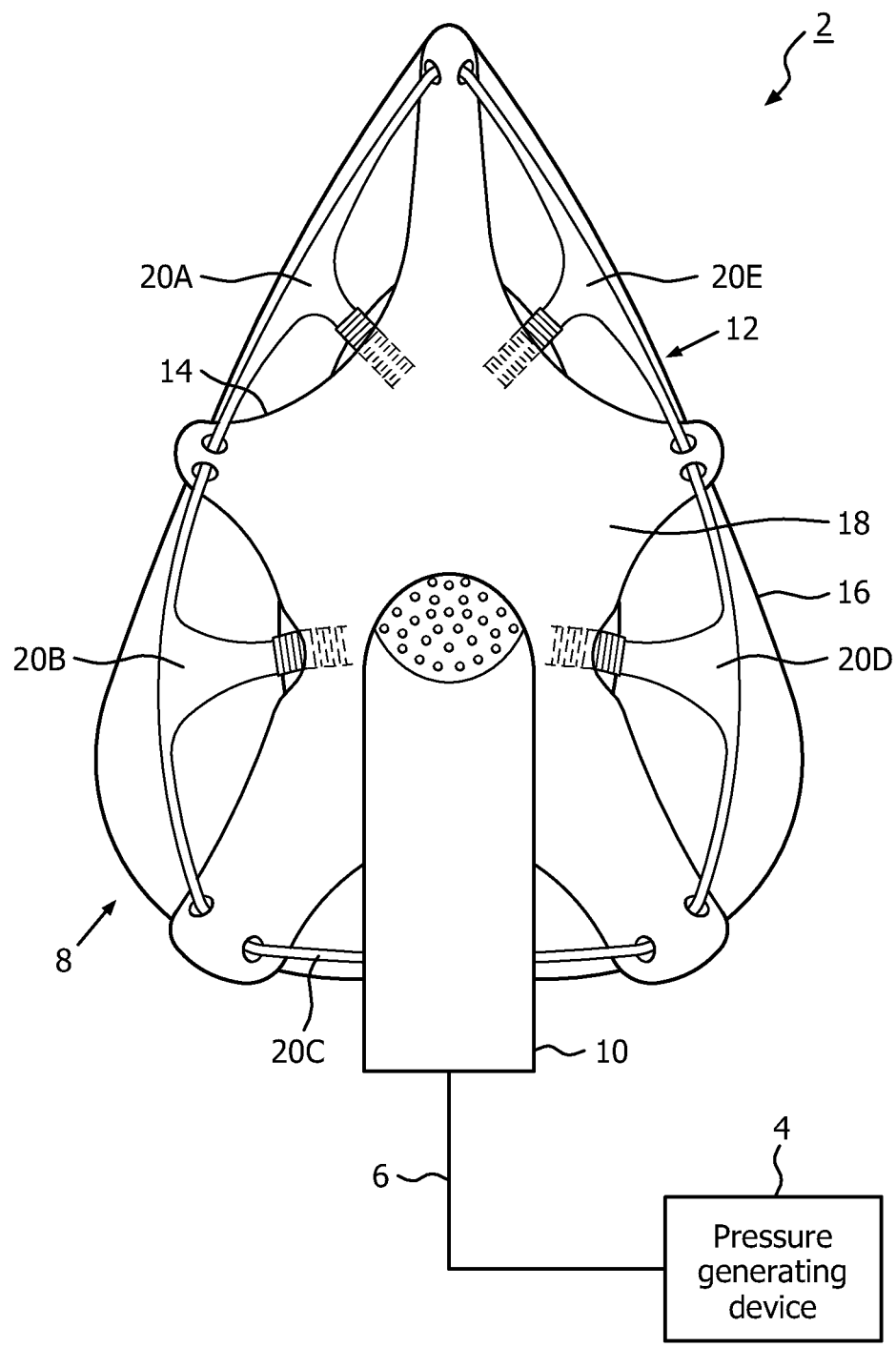
FIGS. 1 and 2 are a schematic diagrams of a system adapted to provide a regimen of respiratory therapy to a patient according to one exemplary embodiment.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment is generally shown in FIGS. 1 (front elevational view) and 2 (side elevational view). System 2 includes a pressure generating device 4, a delivery conduit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

As described in greater detail herein, the size and/or shape of patient interface device 8 is selectively customizable so as to better accommodate a wide variety of user facial geometries. In the exemplary embodiment, patient interface device 8 includes a customizable patient sealing assembly 12, which is shown in front elevational view in FIG. 3. In the illustrated embodiment, patient sealing assembly 12 is a nasal/oral mask. However, other types of patient sealing assemblies, such as, without limitation, a nasal mask, a nasal cushion or a full face mask, which facilitate the delivery of the flow of breathing gas to the airway of a patient, may be substituted for patient sealing assembly 12 while remaining within the scope of the present invention.

In addition, although not shown in the FIGS. for ease of illustration purposes, it is contemplated that patient interface device 8 may include a headgear component for attaching patient interface device 8 to the head of a patient. As is known, such a headgear component may include a number of straps that are coupled to patient sealing assembly 12 by a suitable mechanism, such as a number of looped connectors coupled to appropriate portions of patient sealing assembly 12. It is further contemplated that patient interface device 8 may also include a forehead support member (not shown) as is well known in the art that extends upwardly from patient sealing assembly 12 for providing further support for patient interface device 8 (by engaging the patient's forehead) when it is donned by the patient.

Figure 3:
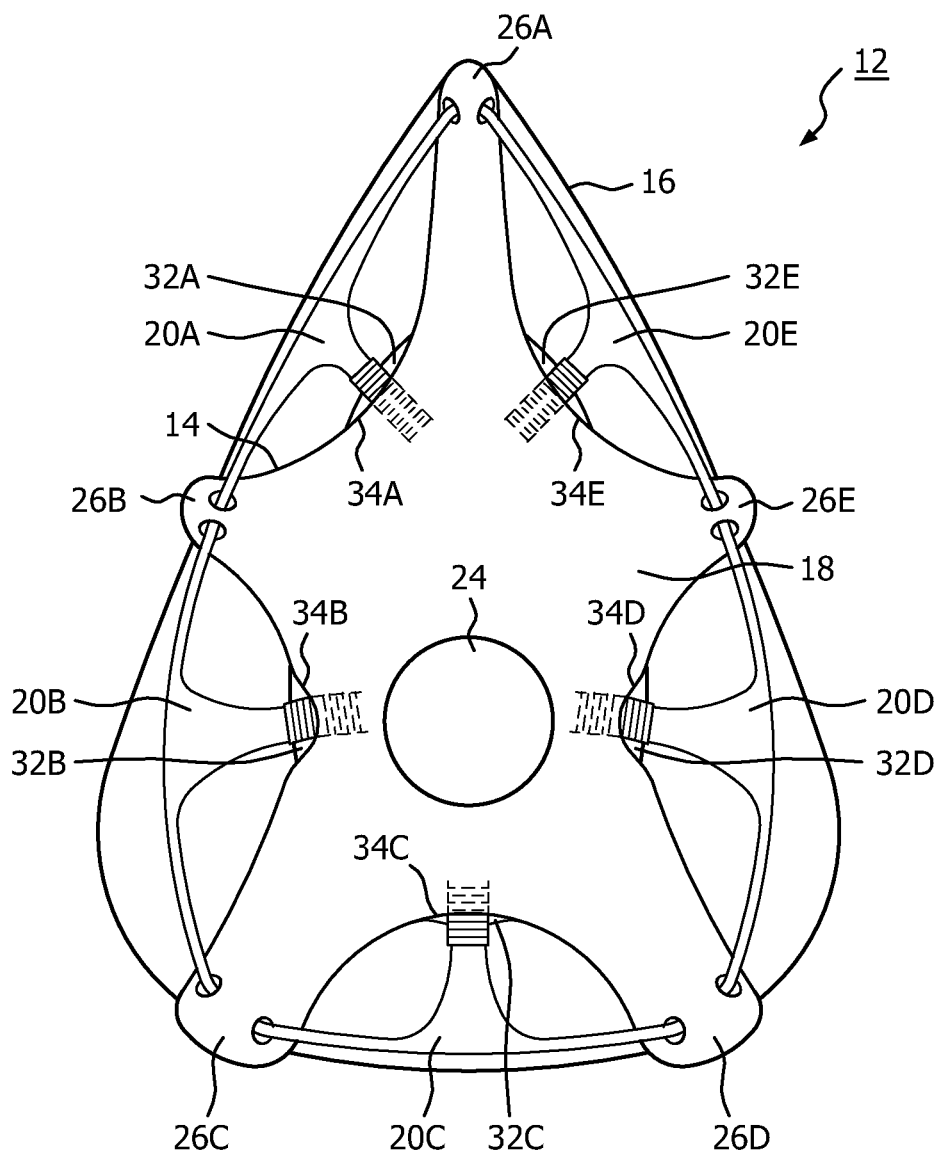
FIG. 3 is a front elevational view of a patient sealing assembly of a patient interface device forming a part of the system of FIG. 2 according to one exemplary embodiment.

Referring to FIGS. 3-6, patient sealing assembly 12 will now be described in detail. As seen in FIG. 3, which is a front elevational view of the exemplary embodiment of patient sealing assembly 12, patient sealing assembly 12 includes a frame assembly 14 and a cushion member 16 coupled to frame assembly 14, each of which is described in greater detail below.

Figure 4A:
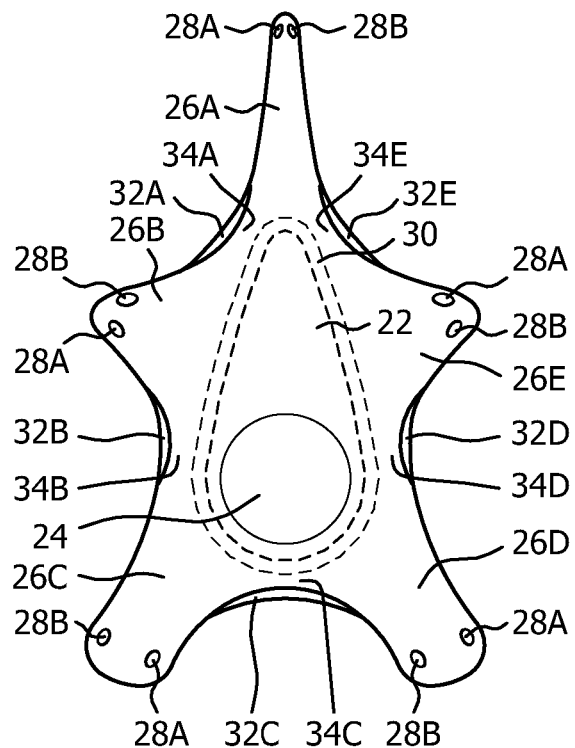
FIGS. 4A and 4B are front and rear elevational views, respectively, of a central frame member of the patient sealing assembly of FIG. 3.
Figure 4B:
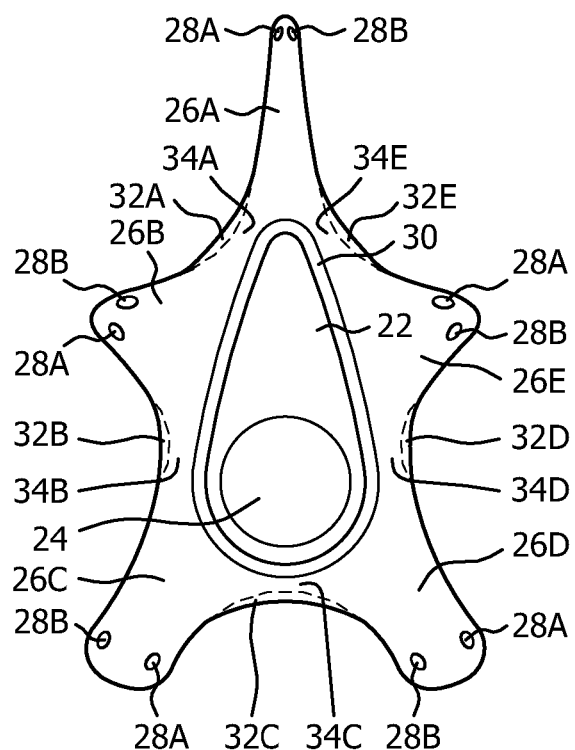

Frame assembly 14 includes a main frame member 18 having a plurality of peg members 20 adjustably coupled to main frame member 18. FIGS. 4A and 4B are front and rear elevational views, respectively, of main frame member 18 according to the exemplary embodiment. In the exemplary embodiment, main frame member 18 is made of a rigid or semi-rigid material, such as, without limitation, an injection molded thermoplastic, silicone or a thermoplastic elastomer. As seen in FIGS. 4A and 4B, in the exemplary embodiment, main frame member 18 generally has a star shape and includes a central portion 22 having an orifice 24 formed therein that is structured to receive fluid coupling conduit 10. Main frame member 18 further includes a plurality of arms 26 extending outwardly from central portion 22. In the illustrated embodiment, main frame member 18 includes five arms 26, labeled 26A-26E. In addition, each arm 26 includes a pair of receiving orifices 28A, 28B located at the tip thereof. Also, a channel 30 is provided in or extending from the rear side of central portion 22. As seen in FIGS. 4A and 4B, channel 30 surrounds orifice 24. The purpose of both receiving orifices 28A, 28B and channel 30 is described elsewhere herein.

Main frame member 18 further includes a plurality of pocket members 32 formed therein. In particular, as seen in FIGS. 4A and 4B, main frame member 18 includes a pocket member 32 located in a region 34 in between each adjacent pair of arms 26. In the illustrated embodiment, main frame member 18 includes five pocket members 26, labeled 26A-26E, each located in one of five regions 34A-34B. The purpose of pocket members 26 is described elsewhere herein. In addition, in the exemplary embodiment, regions 34 are arcuate in shape to provide stability to main frame member 18.

Figure 5A:
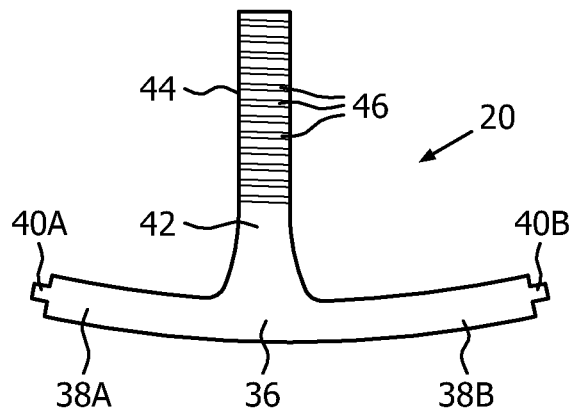
FIGS. 5A-5C are front elevational views of different exemplary embodiments of a peg member of the patient sealing assembly of FIG. 3.

As noted above, frame assembly 14 also includes a plurality of peg members 20. In the illustrated embodiment, frame assembly 14 includes five peg members 20, labeled 20A-20E in FIG. 3. FIG. 5A is a front elevational view of peg member 20 according to the exemplary embodiment. As seen in FIG. 5, peg member 20 has a T-shape and includes an arcuate base member 36 having first and second arms 38A, 38B. Each arm 38A, 38B has a post member 40A, 40B extending from the distal end thereof. Peg member 20 also has a central arm 42 extending from the middle thereof. Central arm 42 includes a rack portion 44 having a plurality of teeth 46. In the exemplary embodiment, peg members 20 are made of a material that, while providing some rigidity, still allows them to flex, particularly at base member 36 (in this regard, peg members 20 are less rigid than main frame member 18). Such material may include a thermoplastic, silicone, or a thermoplastic elastomer having an appropriate durometer to provide for the needed flexibility. In one exemplary embodiment, that durometer is between 20 Shore D and 60 Shore D, and in another exemplary embodiment, that durometer is between 50 Shore D and 90 Shore D.

Figure 5B:
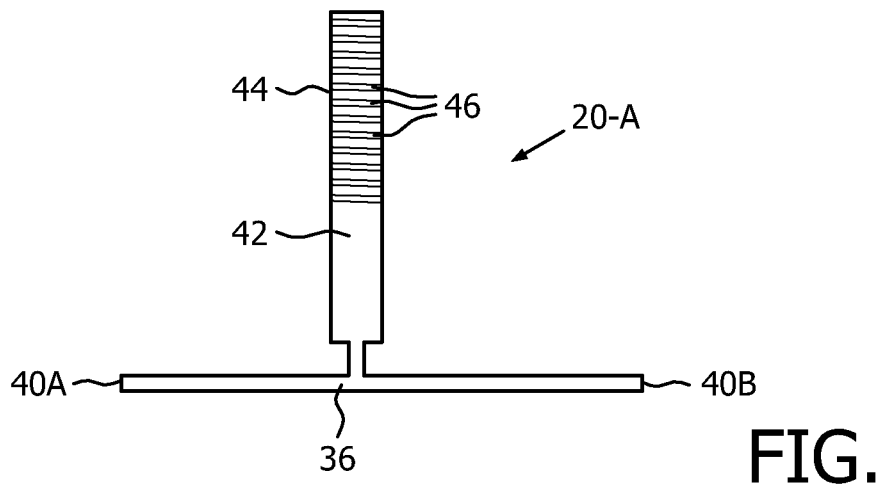
Figure 5C:
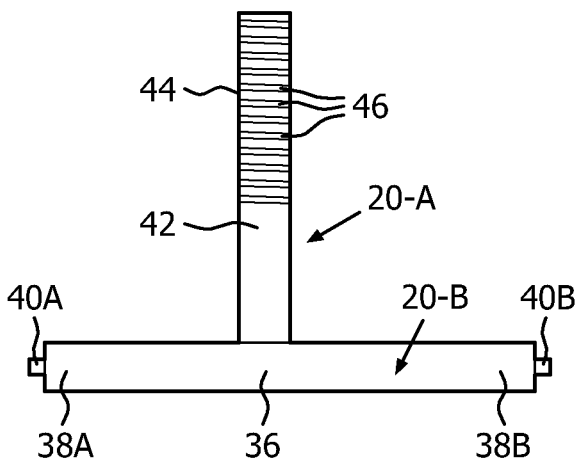

In an alternative embodiment, peg member 20 is made from two materials having different durometers. This is illustrated in FIGS. 5B and 5C. In a first step, the structure/portion 20-A of peg member 20 shown in FIG. 5B is molded using a material having a first durometer, such as a material having a durometer between 50 Shore D and 90 Shore D. Then, the portion 20-B of peg member 20 shown in FIG. 5C is overmolded onto the bottom of the structure/portion 20-A to form base member 36. The portion 20-B is made from a material having a lower durometer (i.e., it is softer) than the structure/portion 20-A, such as a material having a durometer between 20 Shore D and 60 Shore D.

Figure 6A:
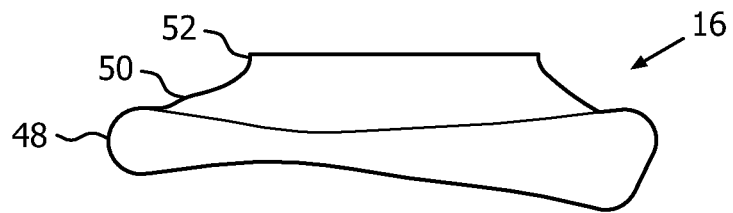
FIGS. 6A and 6B are a side elevational view and a side cross-sectional view, respectively, of a cushion member of the patient sealing assembly of FIG. 3 according to one exemplary embodiment.
Figure 6B:
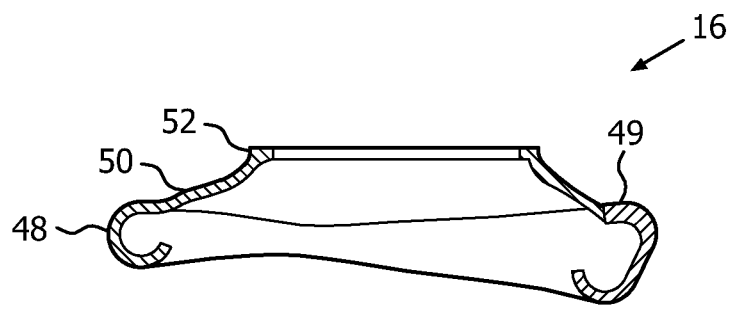

Referring now to FIGS. 6A and 6B, a side elevational view and a side cross-sectional view, respectively, of cushion member 16 are provided. In the exemplary embodiment, cushion member 16 is made of a unitary piece of soft, flexible, cushiony, elastomeric material, such as, without limitation, silicone, an appropriately soft thermoplastic elastomer, a closed cell foam, or any combination of such materials. As seen in FIGS. 6A and 6B, cushion member 16 includes a sealing portion 48 structured to engage the face of the patient and provide an effective seal therewith. The top of sealing member 48 includes a shoulder portion 49, the purpose of which is described elsewhere herein. Cushion member 16 also includes an attachment portion 50 coupled to shoulder portion 49 of sealing portion 48. Attachment portion 50 includes a circumferential lip member 52. Lip member 52 is structured to be received and held within channel 30 of main frame member 18, and thus the shape of lip member 52 matches the shape of channel 30.

Figure 7:
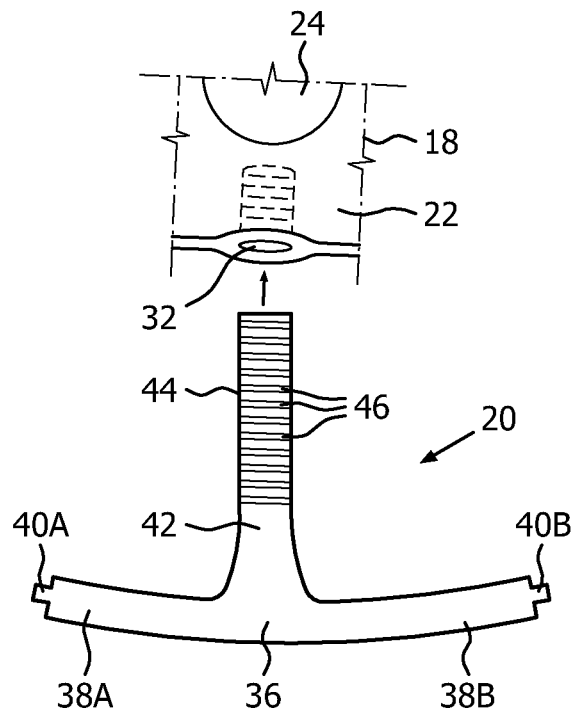
FIG. 7 is a schematic diagram illustrating the assembly of the patient sealing assembly of FIG. 3.

The assembly of frame assembly 14 will now be described. First, cushion member 16 is coupled to the rear of main frame member 18 by inserting lip member 52 into channel 30. Next, each of the peg members 20 is coupled to a respective portion of frame member 18. More specifically, using peg member 20A as an example, post member 40A is inserted into receiving orifice 28A of arm 26A and post member 40B is inserted into receiving orifice 28B of arm 26B. When so inserted, arm 38A of peg member 20A is able to pivot relative to receiving orifice 28A and arm 38B of peg member 20B is able to pivot relative to receiving orifice 28B. In addition, as illustrated in FIG. 7, central arm 42 of peg member 20A is inserted into pocket member 32A.

Figure 2:
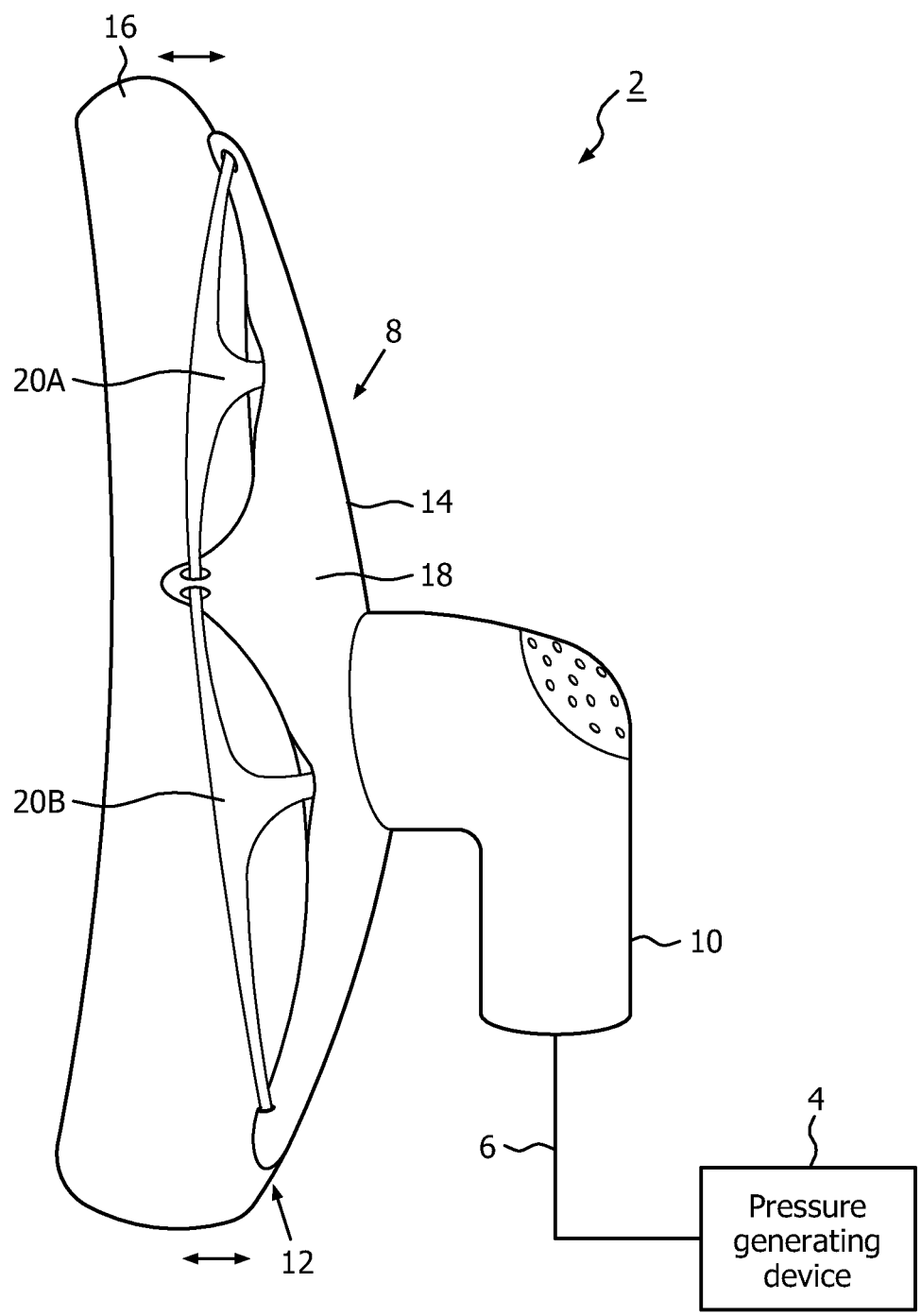

In particular, in the illustrated embodiment, the inside of each pocket member 32 has a toothed structure that is complementary to the teeth 46 of rack portion 44 of each central arm 42 such that the central arm 42 can be freely inserted and moved linearly a certain distance into the pocket member 32 with movement in the opposite direction being resisted/prevented by interaction of the teeth structures. As a result, central arm 42 of peg member 20A, once inserted to the desired depth, will then be securely held in pocket member 32A at that depth. When this insertion occurs, base member 36 of peg member 20A flexes and arms 38A and 38B pivot as described above to accommodate for the movement of peg member 20A. This process is repeated for each of the peg members 20B-20E, with each peg member 20B-20E being inserted to the desired depth. When so assembled, peg members 20A-20E will rest on shoulder portion 49 of sealing portion 48 of cushion member 16 as seen in FIGS. 1 and 2.

Thus, the structure and assembly of frame assembly 14 as just described allows the size and fit of frame assembly 14, and therefore the size and fit of patient interface device 8, to be adjusted in a custom manner by the patient. More specifically, as just described, the patient is able to selectively and independently radially adjust the position of each of the peg members 20A-20E relative to main frame member 18 (i.e., in a direction normal to a plane representing the position of the patient's face when patient interface device 8 is donned by the patient). This selective radial adjustment provides for selective adjustment of the size of frame assembly 14 as indicated by the arrows in FIG. 2. In addition, in the illustrated embodiment, this selective adjustment focuses on the three main areas that leak often occurs (in a nasal/oral mask), namely around the eyes, the cheeks and the chin of the patient (in nasal mask implementation, the selective adjustment would focus on the three main areas that leak often occurs in that type of mask, namely around the eyes, the cheeks and the upper lip of the patient).

Figure 8:
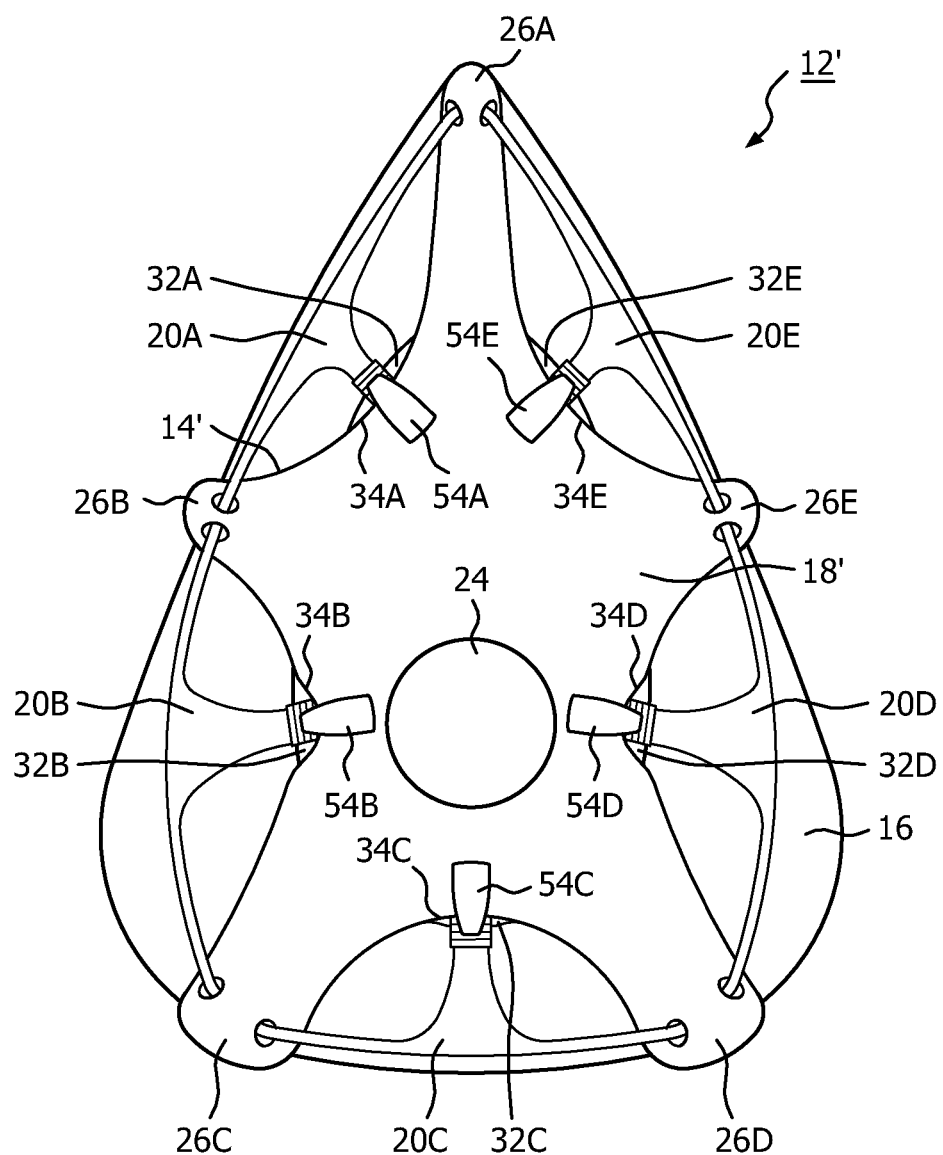
FIG. 8 is a front elevational view of a patient sealing assembly of a patient interface device forming a part of the system of FIG. 2 according to another exemplary embodiment.

FIG. 8 is a front elevational view a patient sealing assembly 12' according to an alternative exemplary embodiment. Patient sealing assembly 12' may be used in place of patient sealing assembly 12 in patient interface device 8 described herein. Patient sealing assembly 12' includes cushion member 16 (as described elsewhere herein) that is coupled (in the manner described elsewhere herein) to an alternative frame assembly 14'.

Figure 9:
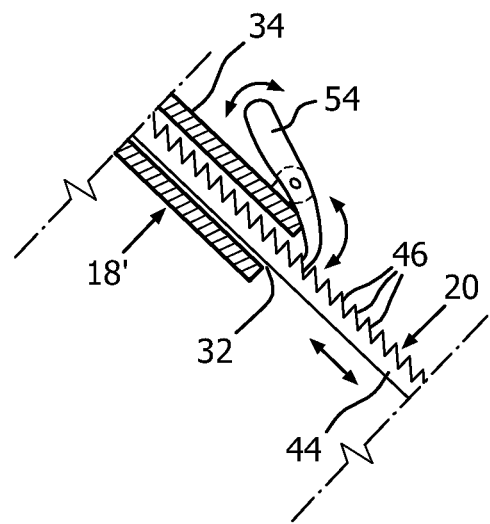
FIG. 9 is a schematic diagram illustrating the operation of the patient sealing assembly of FIGS. 8.

Frame assembly 14' is similar to frame assembly 14 in that it includes peg members 20A-20E as described herein that are coupled to an alternative main frame member 18'. Main frame member 18' is similar in structure to main frame member 18, and like portions/components are labeled with like reference numerals. Main frame member 18', however, includes an alternative mechanism for controlling the insertion, movement and securing in place of peg members 20 within pocket members 32. This alternative mechanism is shown schematically in FIGS. 8 and 9. In particular, each region 34 in between each adjacent pair of arms 26 of main frame member 18' is provided with a pivotable, spring loaded pawl member 54 that is structured to selectively engage teeth 46 of rack portion 44 of peg member 20 when it is inserted into pocket member 32 (in this embodiment, pocket members 32 do not have the complementary toothed structure described elsewhere herein (FIG. 7)). As a result, with the associated pawl member 54 pivoted out of the way (e.g., via a finger pressure applied to pawl member 54 in a known manner), each peg member 20 (and in particular the central arm 42 thereof) may be selectively moved back and forth within the associated pocket member 32 until a desired position therein is achieved. Once the desired position is achieved, the associated pawl member 54 can be released so that it will engage the rack member 44, thereby securing the peg member 20 in the desired position. Thus, by adjusting the peg members 20A-20E as just described, the size and fit of frame assembly 14', and therefore the size and fit of a patient interface device 8 employing the frame assembly 14', may be adjusted in a custom manner by a user.

Figure 10:
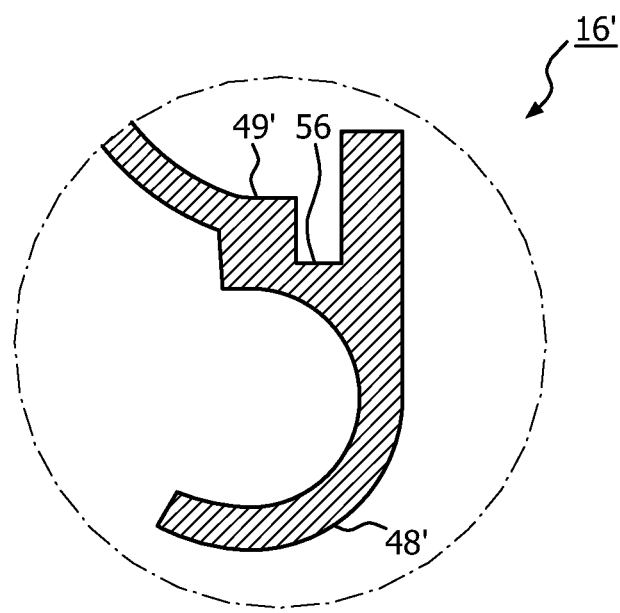
FIG. 10 is a cross-sectional view of a cushion member according to an alternative embodiment that may be used in the patient sealing assembly of FIG. 3.

FIG. 10 is a cross-sectional view of a cushion member 16' according to an alternative embodiment that may be used in pace of cushion member 16. Cushion member 16' includes a sealing portion 48' structured to engage the face of the patient and provide an effective seal therewith. The top of sealing member 48' includes a shoulder portion 49'. As seen in FIG. 10, shoulder portion 49' includes a channel or pocket 56 that extends around the outer periphery of cushion member 16'. Channel or pocket 56 is structured to receive peg members 20A-20E, and in particular the base members 36 thereof, when a patient interface as described herein employing cushion member 16' is assembled. Thus configuration will allow the shape of cushion member 16' to be changed as peg members 20A-20E are selectively adjusted as described elsewhere herein.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
a cushion member structured to engage a face of a patient when the patient interface device is donned by a patient; and
a frame assembly, the cushion member being coupled to the frame assembly, the frame assembly including a main frame member having a plurality of pocket members provided therein, and a plurality of peg members coupled to the main frame member, wherein the main frame member includes a central portion and a plurality of frame arms extending outwardly from the central portion, wherein each of the pocket members is located in a region in between an adjacent pair of the frame arms, wherein each peg member includes an arm member that is received and held within a respective one of the pocket members at a user selectable position, and wherein movement of the peg members relative to the main frame member adjusts a size and/or shape of the patient interface device.

2. The patient interface device according to claim 1, wherein the main frame member has a star shape and the plurality of frame arms comprises five frame arms.

3. The patient interface device according to claim 1, wherein each of the peg members has a T-shape and includes a base member from which the arm member of the peg member extends, wherein the base member includes a first side arm and a second side arm, and wherein, for each of the peg members, the first side arm is coupled to a first one of the frame arms of an adjacent pair of frame arms and the second side arm is coupled to a second one of the frame arms of the adjacent pair of frame arms.

4. The patient interface device according to claim 3, wherein the base member of each of the peg members is generally arcuate in shape.

5. The patient interface device according to claim 3, wherein, for each of the peg members, the first side arm is pivotably coupled to the first one of the frame arms of the adjacent pair of frame arms and the second side arm is pivotably coupled to the second one of the frame arms of the adjacent pair of frame arms.

6. The patient interface device according to claim 5, wherein, for each of the peg members, the first side arm is received in a first orifice provided in the first one of the frame arms of the adjacent pair of frame arms and the second side arm is received in a second orifice provided in the second one of the frame arms of the adjacent pair of frame arms.

7. The patient interface device according to claim 1, wherein each region in between each adjacent pair of the arms is arcuate in shape.

8. The patient interface device according to claim 1, wherein the arm member of each peg member includes a rack portion having a plurality of teeth that are structured to cooperate with a corresponding structure of the pocket member in which the arm member is received to hold the arm member in place at the user selectable position.

9. The patient interface device according to claim 1, wherein the arm member of each peg member includes a rack portion having a plurality of teeth, wherein the main frame member includes a plurality of pawl members, each of the pawl members being associated with a respective one of the pocket members and being structured to selectively engage the rack portion of the arm member received in the one of the pocket members.

10. The patient interface device according to claim 1, wherein each of the peg members rests on a shoulder portion of the cushion member.

11. The patient interface device according to claim 1, wherein each of the peg members has a T-shape and includes a base member coupled to the arm member of the peg member, wherein the base member of each peg member is received within a pocket provided in a shoulder portion of the cushion member.

12. The patient interface device according to claim 1, wherein each of the peg members has a T-shape and includes a base member coupled to the arm member of the peg member, wherein each are arm member is made of a material having a first durometer, and wherein each base member includes a material having a second durometer that is lower than the first durometer.

13. A method of customizing a patient interface device that includes a cushion member and a frame assembly, the cushion member being coupled to the frame assembly, the frame assembly including: (i) a main frame member having a plurality of pocket members provided therein, the main frame member including a central portion and a plurality of frame arms extending outwardly from the central portion, each of the pocket members being located in a region in between an adjacent pair of the frame arms, and (ii) a plurality of peg members coupled to the main frame member, the method comprising:
for each of the peg members, inserting an arm member of the peg member into a respective one of the pocket members and moving the arm member to a user selectable position.

14. The method according to claim 13, further comprising, for each of the peg members, securing the arm member in place at the user selectable position.

15. The method according to claim 13, wherein the arm member of each peg member includes a rack portion having a plurality of teeth that are structured to cooperate with a corresponding structure of the pocket member in which the arm member is received to secure the arm member in place at the user selectable position.

16. The method according to claim 13, wherein the arm member of each peg member includes a rack portion having a plurality of teeth, wherein the main frame member includes a plurality of pawl members, each of the pawl members being associated with a respective one of the pocket members and being structured to selectively engage the rack portion of the arm member received in the one of the pocket members to secure the arm member in place at the user selectable position.

* * * * *